United States Patent [19]
Babirad et al.

[11] Patent Number: 4,852,969
[45] Date of Patent: Aug. 1, 1989

[54] SILYL 2-AMIDOACETATE AND SILYL 3-AMIDOPROPIONATE COMPOSITIONS AND OPTICAL FIBER MADE THEREFROM

[75] Inventors: Stefan A. Babirad, Minneapolis; Fredrick Bacon, St. Paul; Steven M. Heilmann, Afton; Larry R. Krepski, White Bear Lake; Andrew S. Kuczma, Clinton; Jerald K. Rasmussen, Stillwater, all of Minn.

[73] Assignee: Minnesota Mining and Manufacturing Company, St. Paul, Minn.

[21] Appl. No.: 169,377

[22] Filed: Mar. 17, 1988

[51] Int. Cl.$^4$ ............................ G02B 6/02; G02B 1/04
[52] U.S. Cl. .................................... 350/96.34; 544/69
[58] Field of Search .................... 350/96.34; 544/69; 525/308, 279, 304, 309, 176, 183

[56] References Cited

U.S. PATENT DOCUMENTS

| | | |
|---|---|---|
| 4,229,339 | 10/1980 | Bentley et al. ............... 525/183 X |
| 4,511,209 | 4/1985 | Skutnik ......................... 350/96.34 |
| 4,695,608 | 9/1987 | Engler et al. ................. 525/308 |

OTHER PUBLICATIONS

E. V. Kukharskaya and A. D. Fedoseva, *Russ. Chem. Rev.*, 32, 490 (1963).
S. Fordham, "Silicones", George Newnes Ltd.: London, p. 33 (1960).
"Optical Fiber Telecommunication", edited by S. E. Miller and A. G. Chynoweth, Academic Press: New York, 1979; Chapter 10.
A. Sartre, et al., *J. Non-Cryst. Solids*, 66, 467 (1987), Optical Fiber: study of the incorporation of off Groups in A. CVD-Silica Preform.
J. P. Blitz, et al., *J. Am. Chem. Soc.*, vol. 109, No. 23, 109 7141 (1987), Ammonia-Crystalyzed Silylation Reaction of Cab-O14 S. with Methoxymethylsilanes.

*Primary Examiner*—John D. Lee
*Assistant Examiner*—John Ngo
*Attorney, Agent, or Firm*—Donald M. Sell; Walter N. Kirn; Lorraine R. Sherman

[57] ABSTRACT

The present invention provides novel silyl 2-amidoacetates and silyl 3-amidopropionates which are the reaction products of azlactone and silanol reactants. The novel products result from nucleophilic addition of a soluble or insoluble, low or high molecular weight reactant containing one or more silanol groups and a soluble or insoluble, low or high molecular weight reactant containing one or more azlactone groups. The reaction products provide for high adhesion between the siliceous and azlactone reactants, as would be useful as protective coatings particularly on silicon-containing materials. It has been recognized in the present invention that silyl 2-amidoacetates and silyl 3-amidopropionates are useful linkages between silanol and azlactone derived materials.

26 Claims, No Drawings

SILYL 2-AMIDOACETATE AND SILYL 3-AMIDOPROPIONATE COMPOSITIONS AND OPTICAL FIBER MADE THEREFROM

FIELD OF THE INVENTION

This invention relates to novel silyl 2-amidoacetate and silyl 3-amidopropionate compositions that result from the reaction of azlactones and silanols. These reaction products provide for excellent adhesion in the form of covalent bonding to silicon based surfaces, polymers, and compounds. The reaction products find use as protective coatings particularly on silicon-containing materials. They are especially useful as a means of providing well-adhering claddings to siliceous cores for light transmission in a fiber optics construction.

BACKGROUND OF THE INVENTION

The development of fibers which are capable of transmitting light over long distances with relatively low losses began in the mid-to-late 1960's. What has evolved are fiber optics constructions which consist of at least two and generally three components, namely a core, a cladding, and, optionally, a protective coating for the cladded core. The core, which actually performs the light transmitting function, is generally either siliceous glass or an amorphous organic polymer and is physically located at the center of the construction. In order to avoid excessive losses of light in a transverse direction, the core must be coated of "clad" with a material that possesses a refractive index lower than that of the core. This cladding material can be an organic polymer, and because of their relatively low refractive indices, fluorinated polymers and polysiloxanes have emerged as important cladding materials. In addition to proper light handling characteristics, other desirable features of polymeric claddings are thermal and chemical stablity to include resistance to moisture; low surface tack; toughness and abrasion resistance; and, especially important, a high level of adherence to the core material. Additional information concerning fiber optical constructions may be obtained from a book entitled "Optical Fiber Telecommunication", edited by S. E. Miller and A. G. Chynoweth, Academic Press: New York, 1979; Chapter 10 by L. L. Blyler, Jr., et al., deals specifically with claddings and is incorporated as a general reference.

As a general rule, silanol groups reduce the light transmitting qualities of a siliceous core and it is desirable to minimize their concentration. What is apparent from references such as A. Sartre, et al., *J. Non-Cryst. Solids*, 66, 467 (1987), however, is that despite efforts to eliminate silanol groups from siliceous cores, silanol groups persist in low concentration, especially on the core surface. Therefore, as a siliceous molten core emerges from the furnace of a typical draw tower arrangement for preparing optical fibers, the external surface of the core contains silanol groups or will soon develop them.

Attempts to covalently bond to a siliceous substrate (especially glass) have largely involved reactions of alkoxysilanes with surface silanol groups as depicted in equation (1), and a recent paper by J. P. Blitz, et al., *J. Am. Chem. Soc.*, 109 7141 (1987) is cited as a general reference examining the various possible linkages and experimental techniques utilized to probe the nature of the surface reaction.

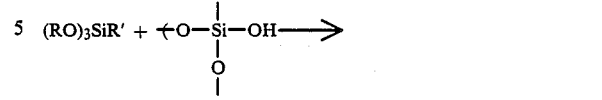

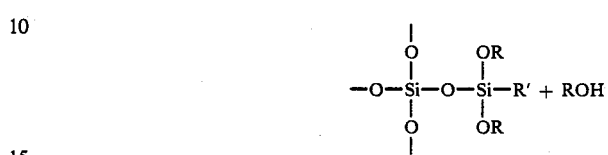

Heterogeneous
Siliceous
Reactant
(HSR)

While the product of equation (1) is relatively stable and chemically inert, there is a problem in that at least one molecule of an alcohol (ROH), which somehow must be removed from the system, is produced for every linkage formed. Removal of the alcohol can be a significant problem when relatively hydrophobic polymers are involved. These polymers do not allow facile passage and removal of the alcohol molecule. The presence of residual alcohol can lead to voids and imperfections in a resultant coating and can oftentimes be a problem with an alkoxysilane/fluoropolymer cladding of a siliceous optical fiber core as described in U.S. Pat. No. 4,511,209.

It is known in the art that silanol groups can be acetylated by conventional acetic anhydride or acetyl chloride reagents to yield the corresponding silyl acetates of equation (2), and a review article by E. V. Kukharskaya and A. D. Fedoseva, *Russ. Chem. Rev.*, 32, 490 (1963) is cited for general reference.

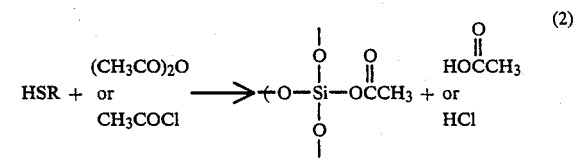

The silyl acetate products are described as being very moisture sensitive and more hydrophobic than the original HSR. In addition, S. Fordham, "Silicones", George Newnes Ltd.: London, p. 33 (1960) indicates that the silyl acetate groups are not very thermally stable, reverting bimolecularly to disiloxane and acetic anhydride.

It is believed that the reaction of an azlactone and a silanol group to afford a silyl 2-amidoacetate has not been previously reported.

SUMMARY OF THE INVENTION

Briefly, the present invention provides novel silyl 2-amidoacetates and silyl 3-amidopropionates. They are the reaction products of azlactone and silanol reactants. The novel products result from nucleophilic addition of a soluble or insoluble, low or high molecular weight reactant containing one or more silanol groups and a soluble or insoluble, low or high molecular weight reactant containing one or more azlactone groups. The reaction products provide for high adhesion between the siliceous and azlactone reactants, as would be useful to secure a cladding material to a siliceous core in a fiber optics construction. It has been recognized in the present invention that silyl 2-amidoacetates and silyl 3-amidopropionates are useful linkages between silanol and azlactone derived materials.

In this application:

"silyl 2-amidoacetates" and "silyl 3-amidopropionates" mean those structures of Formula III in which n=0 and 1, respectively; although IUPAC nomenclatue would dictate complex names for these materials, in the interest of simplicity, the commonly used names "acetate" and "propionate" are employed herein;

"alkyl" means the monovalent residue remaining after removal of a hydrogen atom from a linear or branched chain hydrocarbon having 1 to 14 carbon atoms;

"cycloalkyl" means the monovalent residue remaining after removal of a hydrogen atom from a cyclic hydrocarbon having 3 to 12 carbon atoms;

"lower alkyl" means $C_1$ to $C_4$ alkyl;

"aryl" means the monovalent residue remaining after removal of a hydrogen atom from an aromatic compound (single ring and multi- and fused-cyclic) having 5 to 12 ring atoms and includes substituted aromatics such as lower alkaryl and aralkyl, lower alkoxy, N,N-di(-lower alkyl)amino, nitro, cyano, and lower alkyl carboxylic ester, wherein "lower" means $C_1$ to $C_4$;

"azlactone" means 2-oxazolin-5-one groups of Formula I and 2-oxazin-6-one groups of Formula II;

"silanol" means a compound or a group having the

function;

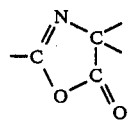  I

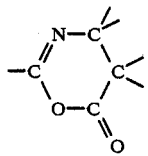  II

"silyloxy" means $(SiO)_x$ which can contain alkyl and aryl groups, and the SiO groups optionally can be interspersed with interpolymerized metal oxides such as oxides of boron, phosphorus, zirconium, molybdenum, and aluminum to form a glass which can be a network of essentially infinite molecular weight; x can have a value of 1 to infinity;

"soluble" and "insoluble" have their classical chemical meanings, i.e., dissolution being a physical and not chemical change, and are utilized because homogeneous/heterogeneous descriptions do not suffice, e.g., silica gel is a heterogeneous, insoluble reactant but homogeneous in appearance when not physically mixed with something else; soluble means at least 0.1 g dissolves in 100 g of any solvent at 23° C.; insoluble means less than 0.1 g dissolves in 100 g of any solvent at 23° C.;

"low molecular weight" refers to soluble compounds of less than 1000 mass units (number average), whereas "high molecular weight" refers to soluble polymers at least 1000 mass units (number average) up to essentially infinite molecular weight and insoluble polymers and materials whose molecular weight are essentially infinite;

"siliceous" means of, relating to, or derived from silica or silicon-containing.

As mentioned above, fiber optics constructions consist of two or three components: a core, a cladding, and optionally a protective coating. Since the external surface of the siliceous core contains silanol groups, it is recognized in the instant invention that the core is an insoluble silanol-functional material capable of reacting with an azlactone. The reaction product silyl 2-amidoacetate or silyl 3-amidopropionate provides well-adhering claddings in a fiber optics construction.

DETAILED DESCRIPTION OF THE INVENTION

The present invention provides novel silyl 2-amidoacetates and silyl 3-amidopropionates which have the general Formula III

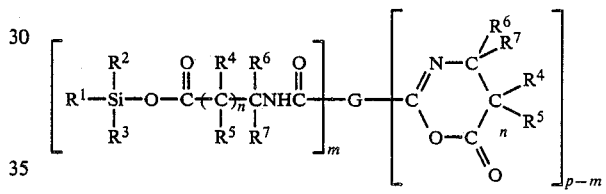

| siliceous material | amido acetate (n = 0) or amido propionate (n = 1) | linking group (m ≥ 2) or terminal group (m = p = 1) | azlactone |

III wherein $R^1$, $R^2$, and $R^3$ can be the same or different and can be alkyl or aryl groups, hydroxy, or silyloxy groups, with the proviso that at most two of the groups can be aryl;

$R^4$ and $R^5$ are independently hydrogen or lower alkyl;

n is 0 or 1;

$R^6$ and $R^7$ are independently an alkyl or cycloalkyl group, an aryl group, or $R^6$ and $R^7$ taken together with the carbon to which they are joined can form a carbocyclic ring containing 4 to 12 ring atoms, with the proviso that only one of $R^6$ and $R^7$ can be aryl;

G is any polyvalent linking group unreactive with azlactone when m is at least 2; or G is any monovalent terminal group unreactive with azlactone when p=m=1;

m can have any positive integral value from 1 to p;

p can have any positive integral value from 1 to infinity when the number of azlactone groups is essentially that value (i.e., infinite) as part of an insoluble, crosslinked network.

G can contain the functionality that may be desired to be imparted to the silanol-bearing substrate provided the functionality is unreactive with azlactone. G can be a simple alkyl or aryl group or G can be quite complex containing multiple functional groups of essentially any kind that is unreactive with azlactone. The molecular weight of G can vary from 15, when G is methyl and p−m=0, to several million (such as 5 million or more) when G is a soluble polymer group, and finally, to infinity, when G is an insoluble, crosslinked polymeric network. G can have bonding capacity of 1, as when it is a terminal group, to essentially infinite bonding capacity as when it is a linking group in a glassy network. Functional groups that can be incorporated in G include one or more of alkyl, aryl, amide, ester, nitrile, nitro, sulfoxide, sulfone, azide, isocyanate, isothiocyanate, tertiary amine, ether, urethane, quaternary ammonium and phosphonium, halogen, and the like, wherein the functional groups requiring substituents are substituted with hydrogen where appropriate or lower alkyl so as not to mask the effect of the functional groups.

When $R^1$, $R^2$, and $R^3$ are silyloxy groups they can be soluble substituted silyloxy groups, i.e., polysiloxane groups with a molecular weight up of about 120 to 500,000 in which the substituents are additional substituted silyloxy groups for $R^1$ and alkyl and aryl for $R^2$ and $R^3$, and insoluble substituted silyloxy groups, i.e., a silica network structure in which $R^1$, $R^2$, and $R^3$ are silyloxy groups, optionally interspersed with interpolymerized oxides of boron, phosphorus, zirconium, molybdenum and aluminum;

The silyl 2-amidoacetates and silyl 3-amidopropionates of the invention are the nucleophilic addition reaction products of a silanol of Formula IV

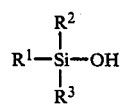

(in which $R^1$, $R^2$, and $R^3$ are as defined above) and an azlactone of Formula V.

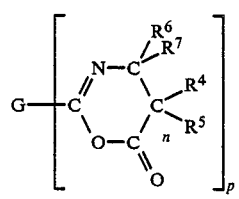

(in which $R^4$, $R^5$, $R^6$, $R^7$, p and G are as defined above) The Formula III reaction products have not previously been reported. The chemical reaction is shown below:

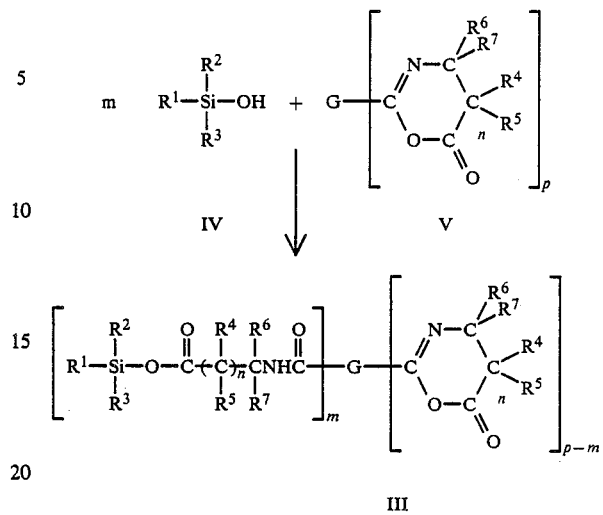

Suitable silanol reactants or substrates of Formula IV of the invention include any soluble or insoluble, low or high molecular weight material that contains at least one Si-OH group: Representative silanol reactants include:

(1) Low molecular weight, soluble silanol materials are compounds of two types: (i) those that have only a transient existence and are essentially non-isolable, as they undergo dehydrative dimerization to disiloxanes at an appreciable rate, and (ii) those that are stable and isolable because at least one of the $R^1$, $R^2$, or $R^3$ (as defined above) is aryl or alkyl (>C-2); this more bulky substitution slows the rate of disiloxane formation considerably. Compounds of the type (i) include trimethylsilanol and ethyldimethylsilanol, and these compounds must be generated in relatively dilute solution (to slow dimerization) and reacted immediately with the azlactone. Compounds of the type (ii) include triethylsilanol, dimethyl (trimethylsilyloxy)silanol, diphenyldisilanol, phenylsilanetriol, and t-butyldimethylsilanol. These compounds are commercially available, for example, from Aldrich Chemical Co., Milwaukee, Wis.

(2) High molecular weight, soluble silanol materials are silanol-terminated polydimethylsiloxanes, polydiphenylsiloxanes, polymethylphenylsiloxanes, and copolymers containing both dimethyl- and diphenylsiloxane units. These materials are available commercially from Petrach Systems, Bristol, Pa. with molecular weights up to 500,000 and are commonly utilized as intermediates in so-called RTV (room temperature vulcanizeable) silicone formulations.

(3) Insoluble silanol materials possessing essentially an infinite molecular weight are any crosslinked silica network structure that contains a silanol group at an interface where contact and reaction with an azlactone is possible. These materials are the Heterogeneous Siliceous Reactants (HSRs) referred to earlier. Such materials include but are not limited to crystalline silicas such as quartz; microcrystalline silicas such as flint and diatomaceous earch; non-crystalline silicas such as vitreous silicas, amorphous silicas, colloidal silicas, silica gels, precipitated silicas, fumed silicas, and hydrous silicas (clays). These are available commercially from many sources such as Nalco Chemical Co., Oak Brook, Ill., and Cabot Cororation, Boston, Mass. It is also recognized as within the scope of the invention that other elements besides silicon and oxygen may be present within the insoluble network structure such as aluminum, sodium, phosphorus, boron, molybdenum, magnesium, and the like.

Suitable azlactone reactants of the invention include any soluble or insoluble, low or high molecular weight material that contains at least one azlactone group. 2-Vinyl-4,4-dimethylazlactone is commercially available from SNPE, Paris, France. When the value of p in Formula V is one, the azlactone group, when reacted, serves primarily to covalently link the silanol substrate with the G group, and the property or modification desired to be imparted to the silanol reactant must be present in G. G may contain one or more functional groups which themselves do not react with the azlactone including alkyl, aryl, amide, ester, nitrile, nitro, sulfoxide, sulfone, azide, isocyanate, isothiocyanate, tertiary amine, ether, urethane, quaternary ammonium and phosphonium, halogen, and the like, wherein the functional groups requiring substituents are substituted with hydrogen where appropriate or lower alkyl so as not to mask the effect of the functional groups. When the value of p in Formula V is not one, the G group may provide both the modifying functional groups or the linkage to other azlactone groups or both. This duality of purpose is especially true with high molecular weight, 2-alkenyl azlactone-containing copolymeric G groups. The nucleophilic addition reaction, especially with an insoluble silanol reactant, occurs at an interface and is non-stoichiometric with regard to the azlactone groups present, i.e., a portion of the azlactone groups will remain unreacted and $p-m \neq 0$. The useful amounts of silanol reactant to azlactone reactant can be in the range of 0.1 to 99.9 equivalents to 99.9 to 0.1 equivalents, preferably 1:99 to 99:1 equivalents, more preferably 10:90 to 90:10. Representative azlactone materials include:

(1) Low molecular weight, soluble azlactone materials include monoazlactones such as 2-alkyl and 2-aryl substituted azlactones, optionally containing the aforementioned functional groups, and polyazlactones of the type disclosed in U.S. Pat. No. 4,485,236 (incorporated by reference) as well as those reported in the general literature such as those reported by S. M. Heilmann, et al., *J. Polymer Sci.: Polymer Chem. Ed.*, 24, 1 (1986), also incorporated by reference. Preferred low molecular weight soluble azlactones include 2-vinyl-4,4-dimethylazlactone, 2-isopropenyl-4,4-dimethylazlactone, 2-vinyl-4,4-dimethyl-2-oxazin-6-one, 2-dodecyl-4,4-dimethylazlactone, 1,4-bis[(4,4-dimethyl-2-oxazolin-5-one-2-yl)]butane, 1,5-bis[2-(4,4-dimethyl-2-oxazolin-5-one-2-yl)ethylthio]-3-oxapentane, and the like.

(2) High molecular weight, soluble azlactone materials include any free radical addition copolymers of 2-alkenyl azlactones such as those disclosed in U.S. Pat. No. 4,304,705, incorporated herein by reference. Not mentioned specifically in that reference but very useful in the present invention are fluorinated comonomers such as 2-fluoroethyl, 2,2,2-trifluoroethyl, 2,2,3,3-tetrafluoropropyl, hexafluoroisopropyl, 1,1-dihydroperfluorobutyl, 1H,1H,5H-octafluoropentyl, perfluorocyclohexyl, 1,1-dihydroperfluorooctyl, 1H,1H,2H,2H-heptadecafluorodecyl, and 1H, 1H, 11H-eicosafluoroundecyl acrylates and methacrylates; fluorinated styrenes such as o-, m-, and p-fluorostyrene and pentafluorostyrene; and others. Preferred high molecular weight soluble azlactones include copolymers containing at least one part by weight of an 2-alkenyl azlactone such as 2-vinyl-4,4-dimethylazlactone and vinyl chloride, ethyl acrylate, styrene, methyl methacrylate, the aforementioned fluorinated monomers, and combinations thereof.

(3) Insoluble azlactone materials possessing essentially an infinite molecular weight include those 2-alkenyl azlactone copolymers with the aforementioned mono(ethylenically unsaturated) comonomers and at least one multi(ethylenically unsaturated) comonomer, whose copolymerization results in the joining of polymer chains causing crosslinking and insolubilization. Suitable multi(ethylenically unsaturated) comonomers include but are not limited to those disclosed in U.S. Pat. No. 4,379,201, also incorporated herein by reference. Since these copolymers, once formed, are insoluble and thermosetting, they are generally prepared directly in the end-use configuration. With an insoluble, silanol material, for example, the comonomer formulation leading to the insoluble, azlactone material is often photopolymerized by standard techniques well known in the art directly onto the siliceous reactant. Other insoluble, azlactone materials useful in the present invention include the crosslinked, hydrophilic, azlactone-functional polymer beads disclosed in U.S. Ser. No. 07/025,605, filed Mar. 13, 1987, now U.S. Pat. No. 4,737,560 which is also incorporated herein by reference. Preferred insoluble azlactones include cyclodehydrated products resulting from reverse suspension polymerization of combinations of N,N-dimethylacrylamide, sodium N-acrylamido)methylalanate, and methylenebisacrylamide.

Representative examples of silyl 2-amidoacetate and silyl 3-amidopropionate compositions of the invention include reaction products of all combinations of silanol and azlactone reactants. Representative examples are shown in TABLE I below.

TABLE I

LOW MOLECULAR WEIGHT, SOLUBLE

| Silanol | Azlactone | |
|---|---|---|
| $(CH_3)_3C-\underset{\underset{CH_3}{\mid}}{\overset{\overset{CH_3}{\mid}}{Si}}OH$ | $CH_2=CHC\underset{O}{\overset{N}{\diagup}}\underset{\diagdown O}{\overset{\diagup}{\diagdown}}\underset{CH_3}{\overset{CH_3}{\diagdown}}$ | $C_{12}H_{25}C\underset{O}{\overset{N}{\diagup}}\underset{\diagdown O}{\overset{\diagup}{\diagdown}}\underset{CH_3}{\overset{CH_3}{\diagdown}}$ |
| $(CH_3)_3SiO\underset{\underset{CH_3}{\mid}}{\overset{\overset{CH_3}{\mid}}{Si}}OH$ | $CH_3\underset{O}{\overset{CH_3}{\diagup}}\underset{\diagdown O}{\overset{N}{\diagdown}}C(CH_2)_4C\underset{O}{\overset{N}{\diagup}}\underset{\diagdown =O}{\overset{CH_3}{\diagdown CH_3}}$ | |

TABLE I-continued

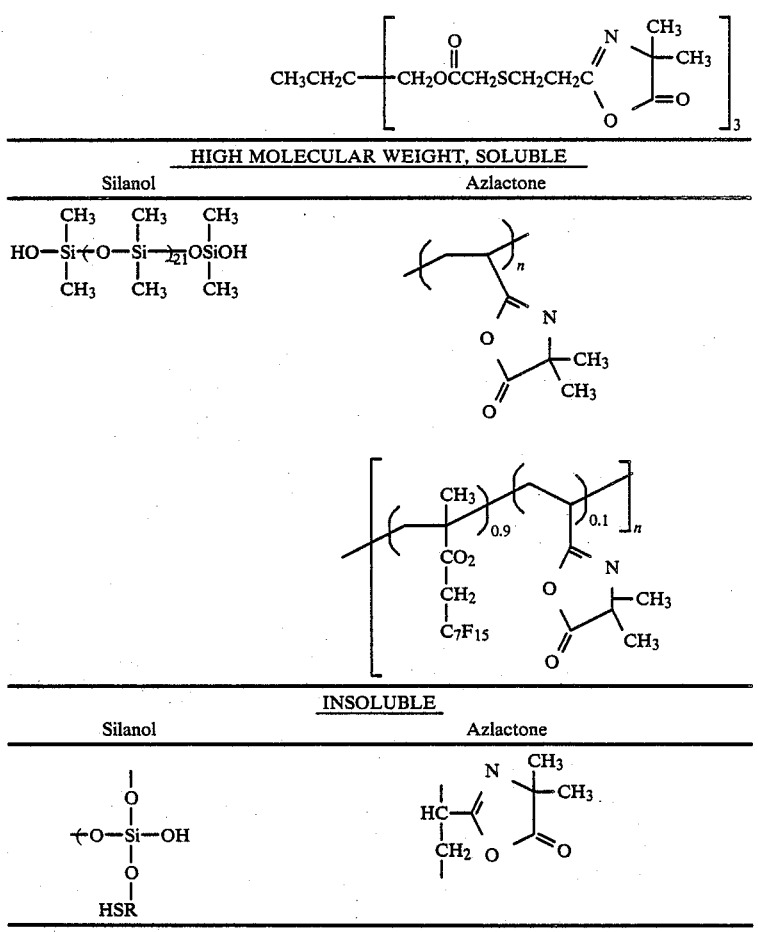

The reaction products of the invention are prepared by mixing the azlactone and silanol reactants, preferably in the absence of solvent and optionally in the presence of a catalyst. Reaction occurs slowly at room temperature, and it is generally desirable to warm the mixture to 25–200° C., preferably 50–200° C., and most preferably from 100–200° C. for a period of a few seconds at higher temperatures to several days when the reaction temperature is relatively low. Cyclic amidine catalysts such as 1,8-diazabicyclo[5.4.0]undec-7-ene (DBU) and 1,5-diazabicyclo[4.3.0]non-5-ene (DBN) in concentrations of from 0.1 to 10.0 mole percent can be employed to hasten completion of the reaction. If solvents are required, they must not react with the azlactone reactant, and suitable solvents include ethyl acetate, toluene, chloroform, dichloromethane, tetrahydrofuran, and fluorinated solvents such as Freon$^R$ 113 (Dupont); when fluorinated azlactone materials are employed. The progress of the reaction and the nature of the reaction product are most easily examined by observing a carbonyl stretching absorption band in the infrared spectrum at about 5.8 micrometers (1720 cm$^{-1}$) for the Si—O—C=O group. Alternatively, NMR is useful, especially with soluble reactants. The terminal Si(CH$_3$)$_2$ $^1$H-NMR resonance of a polydimethylsiloxane silanol-functional material, for example, is shifted downfield 0.2–0.3 ppm relative to starting silanol upon reaction with an azlactone; similarly, $^{29}$Si-NMR results in a downfield shift for the terminal silicon of ca. 4 ppm.

The 2-amidoacetate and 3-amidopropionate groups of the invention function as covalent linkages to modify and adhere silanol and azlactone functional materials. The linkages are useful with all the various reactant combinations but are especially so with insoluble siliceous substrates such as glasses, ceramics, gels, zeolites and the like, and stable modifications of these familiar substrates have a myriad of applications. One such application as a cladding system for a siliceous core in a fiber optics construction is exemplified below.

This invention is particularly useful as a method of providing a cladded optical fiber by coating a glass fiber with a composition comprising an azlactone which can be either a monomer or a polymer. In the case of a monomer, after coating, the cladded fiber can be subjected to UV radiation to effect curing.

Objects and advantages of this invention are further illustrated by the following examples, but the particular materials and amounts thereof recited in these examples, as well as other conditions and details, should not be construed to unduly limit this invention.

EXAMPLE 1

Preparation of t-Butyldimethylsilyl 2-Acrylamido-2,2-dimethylacetate

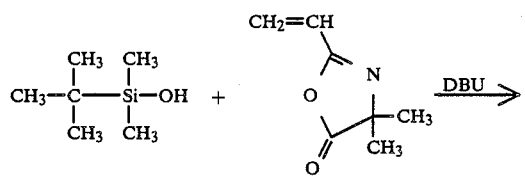

A mixture of 2-vinyl-4,4-dimethylazlactone (VDM) (available from SNPE, Paris, France) (2.78 g, 20 mmoles), t-butyldimethylsilanol (available from Aldrich Chemical Co., Milwaukee, Wis.) (2.64 g, 20 mmoles) and DBU (Aldrich) (150 μL, 1 mmole) was allowed to stand at room temperature for 16 hours. The reaction mixture that resulted was almost completely crystalline. The white solid was slurried with hexanes (30 mL), collected by filtration, and dried in vacuo overnight to provide the desired ester which was identified by spectral analysis.

EXAMPLE 2

Preparation of t-Butyldimethylsilyl 2-Propanamido-2,2-dimethylacetate

In a similar fashion to EXAMPLE 1, t-butyldimethylsilanol was reacted with 2-ethyl-4,4-dimethylazlactone (EDM) (prepared according to J. K. Rasmussen et al., *J. Polymer Sci.: Polymer Chem. Ed.*, 24, 2739 (1986)). No catalyst was required when the reactants were heated at 150° C. for one hour. The white solid was collected as above, and its structure was shown to correspond to the title material by its IR and NHR spectra.

EXAMPLE 3

Preparation of t-Butyldimethylsilyl 2-Benzamido-2,2-dimethylacetate

In a similar fashion to EXAMPLE 2, t-butyldimethylsilanol was reacted with 2-phenyl-4,4-dimethylazlactone (prepared according to H. Rodriguez et al., *Tetrahedron*, 27, 2425 (1971)).

EXAMPLE 4

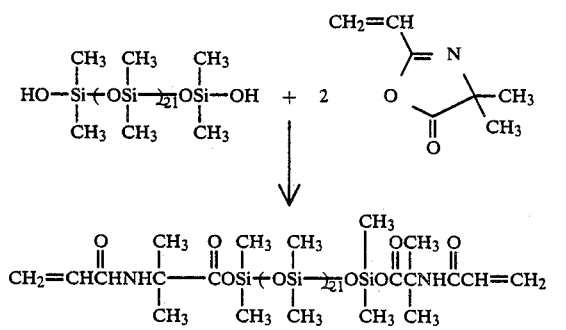

Poly(dimethylsiloxane), silanol-terminated (available from Petrarch Systems, Bristol, Pa.) (silanol equivalent weight 860, 4.38 g, 5.09 mequiv.), VDM (0.71 g, 5.09 mmoles), and 2,6-bis(t-butyl)-4-methylphenol (Aldrich) (5.09 mg as a stabilizer) were charged to an oven-dried vial. The vial was sealed and placed in an oven for one hour equilibrated at 150° C. $^1$H-NHR analysis of a sample of the reaction mixture indicated a 1:1 mixture of starting materials and silyl ester. The remainder of the material was heated an additional two hours at 150° C. to produced a 3:1 mixture of the desired product and starting materials.

EXAMPLE 5

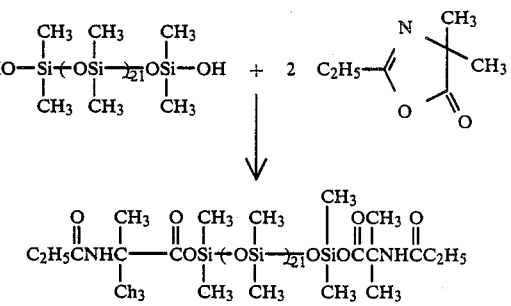

A reaction was conducted similarly to that of EXAMPLE 4, substituting EDM for the VDM reactant. After one hour at 150° C., NMR analysis indicated an 85% conversion to the silyl ester product.

EXAMPLE 6

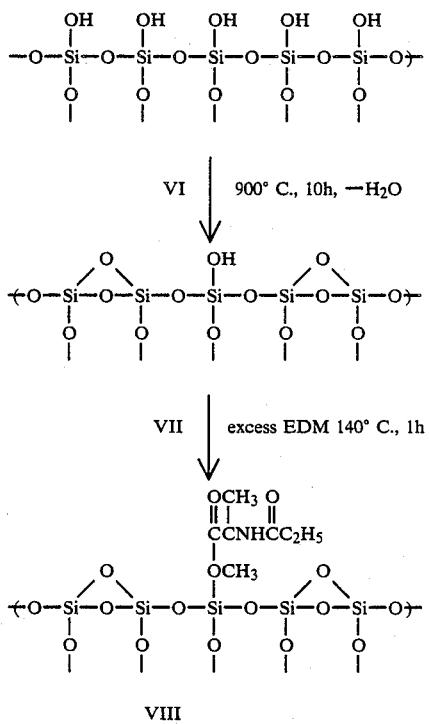

Cabosil M-5 (available from Cabot Corp., Boston, Mass.) was heated at 900° C. for 10 hours at <1 Torr. Upon cooling, the dehydrated, non-sintered silica was sealed and placed in an anhydrous glove box in which all subsequent physical transfers to oven-dried Schlenk glassware were made. This heating condition according to R. K. Iler, "The Chemistry of Silica", Wiley-Interscience: New York, 1979, p. 645, dehydrates silica from a surface hydroxy concentration of 4.5 OH nanometer$^{-2}$, (nm) to 0.66 OH nm$^{-2}$, or 14.7% remaining surface hydroxyl groups. This amount correlates well with the theoretical 13.5% residual groups that remain from vicinal reactions of this type involving 1,3-diol structures (cf. P. J. Flory, *J. Am. Chem. Soc.*, 61, 1518 (1938)). Chemically, the extent of dehydration is fairly accurately depicted above with the HSR of Formula VI yielding the HSR of Formula VII under these thermal conditions in which essentially only isolated silanol groups remain.

As a CONTROL experiment, 1-2 grams of the dried silica were placed in the Schlenk filtration apparatus. The silica as washed with three, 20 mL portions of hexanes (freshly distilled from calcium hydride) under a dry nitrogen atmosphere. After drying at <1 Torr. for 15 minutes, a portion of the silica was mixed with KBr, and the diffuse reflectance FTIR (Fourier transform infrared) spectrum was recorded (500 scans).

The reaction with EDM was accomplished with 1-2 grams of dried silica in the Schlenk apparatus as before, except 4 mL of freshly distilled EDM were added by syringe to completely cover and wet the silica reagent. The entire apparatus containing the heterogeneous mixture was placed in an oven for one hour at 140° C. After cooling, the mixture was filtered and washed with dry hexane in the Schlenk apparatus as before. After drying at <1 Torr. for 15 minutes, the diffuse reflectance FTIR spectrum was again recorded. The most notable observations about the spectra were that the band for the isolated silanol at about 3750 cm$^{-1}$ had almost completely disappeared, and, along with absorption bands for residual and adsorbed EDM, other bands were present which could be assigned to the desired nucleophilic addition product (Formula VIII).

The direct observation of the nucleophilic addition product of an insoluble silanol and EDM is extremely important because EDM is an excellent model for a pendant azlactone on a polymer. The core can simply be regarded as an insoluble, silanol-functional material, for example HSR above, capable of reacting with an azlactone.

EXAMPLE 7

Preparation of the Polymeric Claddings 1,1-Dihydroperfluorooctyl methacrylate (FOM) (available from Monomer-Polymer & Dajac Laboratories Inc., Trevose, Pa.) was shaken with anhydrous potassium carbonate, filtered, and vacuum distilled from copper powder. The colorless middle fraction distilling t 69-71° /1.2-1.5 Torr. was collected and utilized. Bis(4-t-butylcyclohexyl)peroxydicarbohate (Percadox TM 16N; available from Noury Chemical Corp., Burt, N.Y.) and a chlorofluorocarbon solvent (Freon ® 113, E. I. Du Pont de Nemours & Co., Wilmington, Del.) were utilized as received.

A 900 mL glass bottle was charged with FOM (397.36 g), VDM (44.16 g), Freon ® 113 (662.28 g), and Percadox TM 16 N (2.20 g). The solution was sparged briefly with nitrogen, sealed, and the bottle placed in an Atlas Launderometer (available from Atlas Electric Devices Co., Chicago, Ill.) at 43° C. for 24 hours. A viscous, clear copolymer solution resulted, and the copolymer exhibited an inherent viscosity in Freon° 113 at 25° C. of 0.22 dL/g. Similarly, a homopolymer of FOM was prepared as a CONTROL, and the homopolymer inherent viscosity was 0.19 dL/g.

Evaluation of the Polymers as Cladding Materials

The FOM:VDM copolymer solution was applied in a draw tower arrangement similar to that depicted by L. L. Blyler, Jr., et al., CHEMTECH, 680 (1987). The siliceous core consisted of a Diasil rod (available from Mitsubishi Rayon Co., Hiroshima, Japan) heated to 2200° C. and drawn to a diameter of 200 micrometers. Application of the copolymer from solution in a bath coater was followed by passing the cladded core into an oven equilibrated at 200° C. (residence time about 3 seconds). The diameter of the cladding applied under these conditions was about 10 micrometers. The cladded core construction was non-tacky, quite tough, and was able to be repeatedly flexed without causing delamination of the cladding. The cladding was extremely adherent to the core and could not be peeled from it. In contrast, huge sections of cladding were easily removed from a similar cladded core construction prepared with the CONTROL FOM homopolymer. The FOM:VDM cladded core provided a numerical aperature of 0.51 and an attenuation loss (at 812 nm) of 3.6 dB/km when evaluated according to procedures put forth by the American National Standards Institute in "Generic Specifications for Optical Waveguides", EIA-492, April 1985.

Various modifications and alterations of this invention will become apparent to those skilled in the art without departing from the scope and spirit of this invention, and it should be understood that this invention is not to be unduly limited to the illustrative embodiments set forth herein.

We claim:

1. A composition of matter comprising at least one of a silyl 2-amidoacetate and a silyl 3-amidopropionate.

2. The composition of matter according to claim 1 which is the reaction product of a silanol and an azlactone.

3. The composition of matter according to claim 2 further comprising in the range of 0.1 to 10.0 mole percent of a cyclic amidine catalyst.

4. The composition of matter according to claim 2 wherein said silanol has a molecular weight in the range of less than 1000 up to 500,000.

5. The composition of matter according to claim 2 wherein said silanol has an insoluble network structure having an essentially infinite molecular weight.

6. The composition according to claim 5 wherein said network structure further comprises at least one atom selected from the group consisting of aluminum, sodium, phosphorus, boron, molybdenum, and magnesium atoms.

7. The composition of matter according to claim 5 wherein said insoluble silanol is a non-crystalline silica.

8. The composition of matter according to claim 3 where said azlactone is a monoazlactone.

9. The composition of matter according to claim 8 wherein said monoazlactone is a 2-alkyl or 2-aryl substituted azlactone.

10. The composition of matter according to claim 3 wherein said azlactone is a polyazlactone.

11. The composition of matter according to claim 3 wherein said azlactone is 2-alkenyl azlactone or a copolymer thereof.

12. The composition of matter according to claim 11 wherein said copolymeric 2-alkenyl azlactone is prepared from a mono- or multi(ethylenically unsaturated) comonomer.

13. A composition of matter comprising at least one of a silyl 2-amidoacetate and a silyl 3-amidopropionate having the formula:

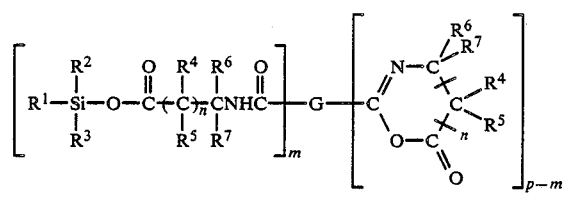

wherein
$R^1$, $R^2$, and $R^3$ are the same or different group and are selected from the class consisting of alkyl and aryl, hydroxy, and silyloxy groups, with the proviso that at most two of the groups are aryl;
$R^4$ and $R^5$ are independently hydrogen or lower alkyl;
n is 0 or 1;
$R^6$ and $R^7$ are independently an alkyl or cycloalkyl group, an aryl or aralkyl group, or $R^6$ and $R^7$, taken together with the carbon to which they are joined can form a carbocyclic ring containing 4 to 12 ring atoms, with the proviso that only one of $R^6$ and $R^7$ can be aryl;
G is any polyvalent linking group unreactive with azlactone when m is at least 2, or G is any monovalent terminal group unreactive with azlactane when p=m=1;
m can have any positive integral value from 1 to p;
p can have any positive integral value from 1 to infinity.

14. The composition of matter according to claim 13 where at least one of $R^1$, $R^2$, and $R^3$ is a soluble or insoluble silyloxy group.

15. The composition of matter according to claim 14 wherein said soluble silyloxy group is a polysiloxane group.

16. The composition of matter according to claim 14 wherein said insoluble silyloxy group is a silica network.

17. The composition of matter according to claim 16 wherein said silica network is interspersed with interpolymerized oxides of at least one of boron, phosphorus, zirconium, molybdenum, and aluminum.

18. The composition of matter according to claim 13 where G comprises at least one functional group selected from the group consisting of alkyl, aryl, amide, ester, nitrile, nitro, sulfoxide, sulfone, azide, isocyanate, isothiocyanate, tertiary amine, ether, urethane, quaternary ammonium and phosphonium, halogen, and the like, wherein the functional groups requiring substituents are substituted with hydrogen where appropriate or lower alkyl so as not to mask the effect of the functional groups.

19. The composition of matter according to claim 13 wherein G has a molecular weight in the range of 15 to 5 million.

20. An optical fiber comprising a silyl 2-amidoacetate or a silyl 3-amidopropionate composition of matter.

21. The optical fiber according to claim 20 wherein said composition is the reaction product of silanol-containing fiber core and an azlactone-containing cladding.

22. The optical fiber according to claim 20 wherein said silyl 2-amidoacetate or silyl 3-amidopropionate has the formula:

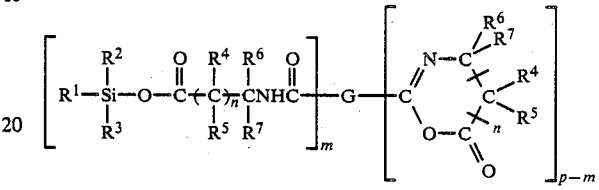

wherein
$R^1$, $R^2$, and $R^3$ are the same or different group and are selected from the class consisting of alkyl and aryl, hydroxy, and silyloxy groups, with the proviso that at most two of the groups are aryl;
$R^4$ and $R^5$ are independently hydrogen or lower alkyl;
n is 0 or 1;
$R^6$ and $R^7$ are independently an alkyl or cycloalkyl group, an aryl or aralkyl group, or $R^6$ and $R^7$ taken together with the carbon to which they are joined can form a carbocyclic ring containing 4 to 12 ring atoms, with the proviso that only one of $R^6$ and $R^7$ can be aryl;
G is any polyvalent linking group unreactive with azlactone when m is at least 2, or G is any monovalent terminal group unreactive with azlactone when p=m=1;
m can have any positive integral value from 1 to p;
p can have any positive integral value from 1 to infinity.

23. The optical fiber according to claim 20 wherein at least one of $R^1$, $R^2$, and $R^3$ is an insoluble silyloxy group.

24. The optical fiber according to claim 23 wherein said insoluble silyloxy group is a silica network.

25. The optical fiber according to claim 24 wherein said silica network is interspersed with interpolymerized oxides of at least one of boron, phosphorus, zirconium, molybdenum, and aluminum.

26. The optical fiber according to claim 24 wherein said network structure further comprises at least one atom selected from the group consisting of aluminum, sodium, phosphorus, boron, molybdenum, and magnesium atoms.

* * * * *

UNITED STATES PATENT AND TRADEMARK OFFICE
CERTIFICATE OF CORRECTION

PATENT NO. : 4,852,969

DATED : August 1, 1989

INVENTOR(S) : Stefan A. Babirad et al.

It is certified that error appears in the above-identified patent and that said Letters Patent is hereby corrected as shown below:

Col. 1, line 30, "of" should read -- or --.

Col. 2, lines 1-15, delete formula (1) and insert therefor --

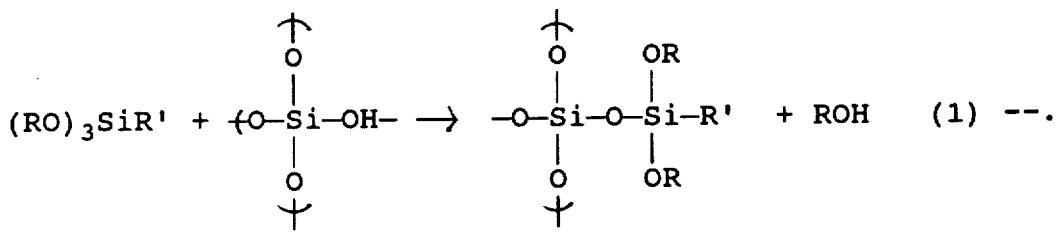

Col. 2, lines 42-48, delete formula (2) and insert therefor --

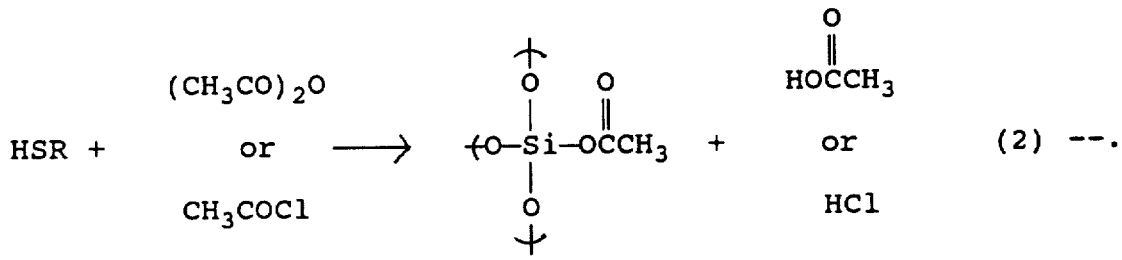

Col. 3, line 31, "means2-oxazolin-5-one" should be -- means 2-oxazolin-5-one --.

UNITED STATES PATENT AND TRADEMARK OFFICE
CERTIFICATE OF CORRECTION

PATENT NO. : 4,852,969

DATED : August 1, 1989

INVENTOR(S) : Stefan A. Babirad et al.

It is certified that error appears in the above-identified patent and that said Letters Patent is hereby corrected as shown below:

Col. 3, line 55, "$(SiO)_x$" should be --$(SiO)_x$--.

Col. 4, lines 29-45, delete formula III and insert --

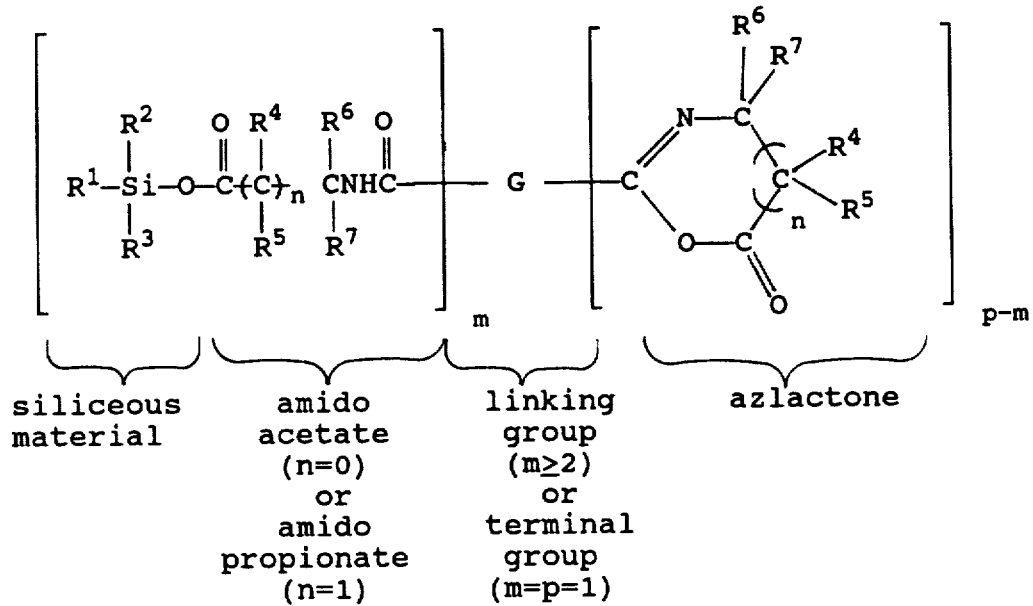

III --.

UNITED STATES PATENT AND TRADEMARK OFFICE
CERTIFICATE OF CORRECTION

PATENT NO. : 4,852,969

DATED : August 1, 1989

INVENTOR(S) : Stefan A. Babirad et al.

It is certified that error appears in the above-identified patent and that said Letters Patent is hereby corrected as shown below:

Col. 5, lines 55-62, delete the formula and insert --

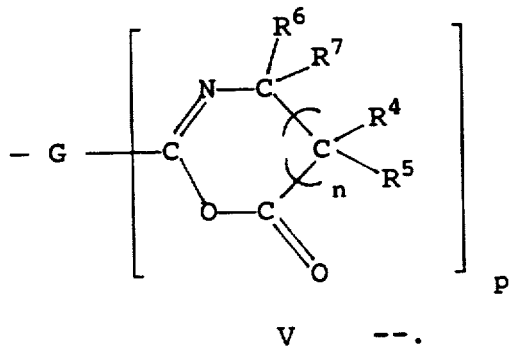

V --.

UNITED STATES PATENT AND TRADEMARK OFFICE
CERTIFICATE OF CORRECTION

PATENT NO. : 4,852,969

DATED : August 1, 1989

INVENTOR(S) : Stefan A. Babirad et al.

It is certified that error appears in the above-identified patent and that said Letters Patent is hereby corrected as shown below:

Col. 6, lines 1-22, delete the chemical reaction and insert --

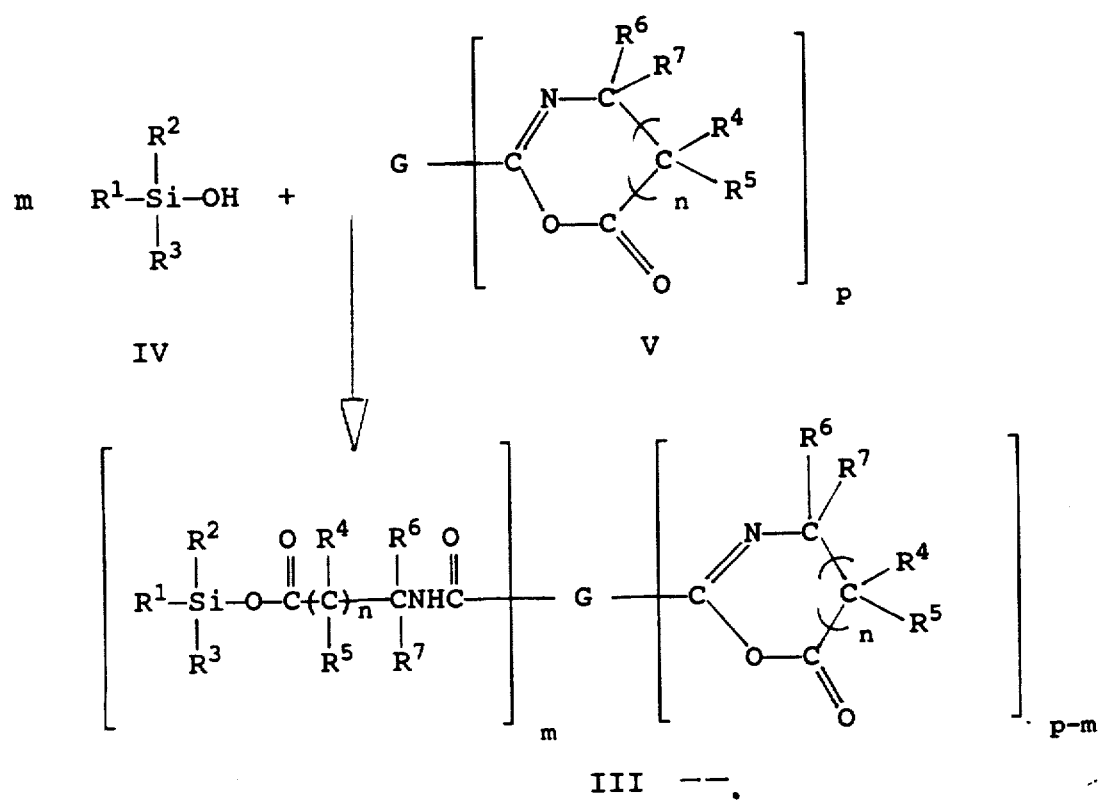

--.

UNITED STATES PATENT AND TRADEMARK OFFICE
CERTIFICATE OF CORRECTION

PATENT NO. : 4,852,969

DATED : August 1, 1989

INVENTOR(S) : Stefan A. Babirad et al.

It is certified that error appears in the above-identified patent and that said Letters Patent is hereby corrected as shown below:

Col. 8, lines 11-12, "1H, 1H, 11H-eicosafluoroundecyl" should read -- 1H,1H,11H-eicosafluoroundecyl --.

Col. 9, Under "INSOLUBLE" delete the formulae titled "Silanol" and "Azlactone" and insert, respectively, therefor --

Silanol

Azlactone

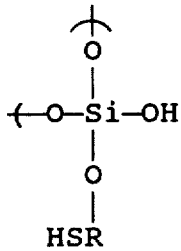
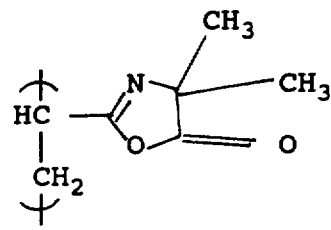

(in which the structures between the parentheses are a partial structure of a crosslinked polymer) --.

Col. 12, line 4, "'H-NHR" should be -- 'H-NMR --.

UNITED STATES PATENT AND TRADEMARK OFFICE
CERTIFICATE OF CORRECTION

PATENT NO. 4,852,969

DATED   August 1, 1989

INVENTOR(S) Stefan A. Babirad et al.

It is certified that error appears in the above-identified patent and that said Letters Patent is hereby corrected as shown below:

Col. 12, line 24, "Ch$_3$" should be -- CH$_3$ --.

Col. 12, lines 32-60, delete formulae VI, VII, and VII, and insert therefor --

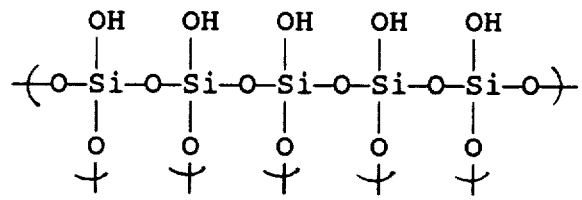

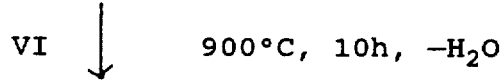   VI   900°C, 10h, −H$_2$O

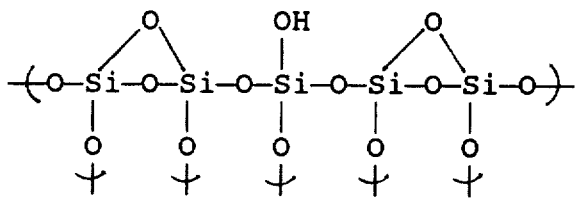

VII   excess EDM
140°C, 1h

UNITED STATES PATENT AND TRADEMARK OFFICE
CERTIFICATE OF CORRECTION

PATENT NO. : 4,852,969

DATED : August 1, 1989

INVENTOR(S) : Stefan A. Babirad et al.

It is certified that error appears in the above-identified patent and that said Letters Patent is hereby corrected as shown below:

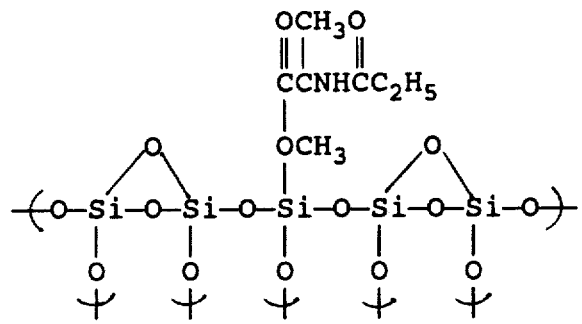

VIII --.

Col. 13, line 54, "distilling t 69-71°" should read -- distilling at 69-71° --.

Col. 13, line 55, "Bis(4-t-butylcyclohexyl)peroxydicarbohate" should be -- Bis(4-t-butylcyclohexyl)-peroxydicarbonate --.

Col. 13, line 67, "Freon°" should be -- Freon$^R$ --.

UNITED STATES PATENT AND TRADEMARK OFFICE
CERTIFICATE OF CORRECTION

PATENT NO. : 4,852,969

DATED : August 1, 1989

INVENTOR(S) : Stefan A. Babirad et al

It is certified that error appears in the above-identified patent and that said Letters Patent is hereby corrected as shown below:

Col. 15, line 33, "azlactane" should be --azlactone--.

Signed and Sealed this

Twenty-first Day of September, 1993

Attest:

BRUCE LEHMAN

Attesting Officer

Commissioner of Patents and Trademarks